United States Patent [19]

Mendiratta

[11] Patent Number: 4,590,303
[45] Date of Patent: May 20, 1986

[54] METHOD FOR MAKING BISPHENOL

[75] Inventor: Ashok K. Mendiratta, Schenectady, N.Y.

[73] Assignee: General Electric Company, Schenectady, N.Y.

[21] Appl. No.: 740,688

[22] Filed: Jun. 3, 1985

[51] Int. Cl.$^4$ .................. C07C 39/12; C07C 39/16
[52] U.S. Cl. ................................. 568/728; 568/727
[58] Field of Search ........................... 568/727, 728

[56]  References Cited
U.S. PATENT DOCUMENTS 3,221,061 11/1965 Grover et al. .................. 568/728
4,308,404 12/1981 Kwantes et al. ................ 568/727
4,308,405 12/1981 Kwantes ......................... 568/727
4,348,542 9/1982 Serini et al. .................... 568/727
4,375,567 3/1983 Faler ............................. 568/727
4,400,555 8/1983 Mendiratta ..................... 568/728

Primary Examiner—Werren B. Lone
Attorney, Agent, or Firm—William A. Teoli; James C. Davis, Jr.; James Magee, Jr.

[57]  ABSTRACT

A method of making bisphenol A from phenol and acetone is provided which allows for the use of reactor acetone feed in the rearrangement reactor. As a result, improved acetone conversion is realized and BPA productivity is enhanced.

5 Claims, 2 Drawing Figures

METHOD FOR MAKING BISPHENOL

BACKGROUND OF THE INVENTION

Prior to the present invention, as shown by Grover et al. U.S. Pat. 3,221,061, directed to a Method for Making Bisphenol A, a rearrangement reactor was used to convert by-product BPA isomers, such as o,p-bisphenol A to p,p-bisphenol A to improve overall BPA product yield. As shown by Mendiratta, U.S. Pat. No. 4,400,555, assigned to the same assignee as the present invention and incorporated herein by reference, improved reactant effluent product distribution was achieved in bisphenol A synthesis by using multiple acetone injection in an ion exchange catalyzed BPA synthesis process.

The present invention is based on my discovery that enhanced acetone conversion and improved BPA productivity can be achieved in bisphenol A synthesis by diverting part of the acetone, normally fed to the condensation reactor, to the rearrangement reactor. I have further found that if the amount of acetone diverted is held within certain limits, as defined hereinafter, the product distribution of the condensation reactor effluent can be substantially maintained. Improved efficiency in the production of bisphenol A is realized as the result of such higher acetone conversion.

STATEMENT OF THE INVENTION

There is provided by the present invention a process for making bisphenol A by feeding phenol and acetone into a condensation reactor at a temperature of about 50° C. to about 120° C. in the presence of an ion exchange catalyst to produce a mixture of bisphenol A, phenol and bisphenol A isomers, which thereafter are separated in a crystallizer to provide the recovery of bisphenol A and the recycling back to the condensation reactor of a mixture of phenol and bisphenol A isomers, through the rearrangement reactor, which comprises the improvement of diverting part of the acetone initially fed to the condensation reactor to the rearrangement reactor, whereby an improvement in overall acetone conversion is achieved, while the product distribution of the condensation reactor effluent is substantially maintained.

The process of the present invention can be conducted under substantially anhydrous conditions where the water resulting from the condensation reaction and rearrangement reaction is less than 2% and preferably less than 1.5% in the reaction mixture. Mole ratios of phenol to acetone which are used in the practice of the method of the invention, can be from about 2:1 to about 30:1, and preferably about 10:1.

Conventional ion-exchange resin catalysts can be used in the practice of the method of the present invention. For example, strong-acid ion exchange resins, including resins or polymers can be used which have a plurality of appended sulfonic acid groups. Some of these ion exchange resins are, for example, sulfonated polystyrene or poly(styrene-divinyl-benzene)copolymers and sulfonated phenolformaldehyde resins. Specific examples of commercially available resins which can be used are Amberlite ® or Amberlyst ® manufactured by Rohm and Haas, Dowex ® manufactured by Dow Chemical Company, Permutit QH ® manufactured by Chemical Process Company, C-20 ® manufactured by Chemical Process Company and DUOLITE ® manufactured by Diamond Shamrock. As stated before, the acid ion exchange resins can be partially modified by reacting the acidic groups with mercapto alkyl amines, by partially esterifying the acid resins with a mercapto alcohol, or with an alkyl amine precursor such as thiazolidines. The unmodified ion-exchange resins generally have an ion-exchange capacity preferably of at least about 2.0 milliequivalents H+, with exchange capacities in the range of from about 3 to about 5 milliequivalents of H+ per gram of dry resin. About 5% to about 35% of more, preferably from about 10% to about 25% of acid sites are modified by reacting the acid sites with a mercapto group.

It has been found that effective results can be achieved even if reaction times in the individual reaction zones under steady state reaction conditions are varied widely. The reaction can be carried out at between about 50° C. and about 120° C., and preferably between about 60° C. and 80° C. The weight hourly space velocity (WHSV) of the reactor feed to the condensation reactor and the rearrangement reactor may vary within the limits of from about 0.05 to about 15 parts by weight of feed per part of catalyst per hour. There can be diverted to the rearrangement reactor, from about 5% to 70% by weight of acetone feed per hour, based on the weight of total acetone feed to the condensation reactor per hour, and preferably from 10% to 40% by weight.

The process of the invention is applicable to the preparation of bis(hydroxyphenyl)compounds and such compounds are derived by substituting or including, in addition to phenol, other phenolic reactants including ortho- and meta-cresol; 2,6-dimethylphenol; ortho-secondary butylphenol; ortho-tertiary butylphenol; 2,6-ditertiary butylphenol; 1,3,5-xylenol, tetramethylphenol; 2-methyl-6-tertiary butylphenol; ortho-phenylphenol; ortho-metachlorophenol; ortho-bromophenol; t-chloro-ortho-cresol; 2,6-dichlorophenol. Phenol is the preferred phenolic reactant.

In addition to acetone, the process of the present invention can be carried out by substituting aldehydes or other ketones for acetone. Specific examples include methyl ethyl ketone, methyl propyl ketone, acetophenone, methyl vinyl ketone, cyclopentanone, cyclohexanone, benzophenone, hexafluoracetone, etc.

DESCRIPTION OF THE DRAWING

In order that those skilled in the art will be better able to understand the practice of the present invention, reference is made to the drawings.

There is shown in FIG. I, feed lines for phenol at 10, acetone at 20 and recycled phenol/p,p-bisphenol A/o,p-bisphenol A and steady state reaction by-products at 30 which are directed to the condensation reactor maintained at a temperature of about 60° C. to 80° C. The effluent from the condensation reactor is passed at 40 to an acetone/water/phenol evaporator unit where anhydrous phenol and acetone are recovered and recycled back to the condensation reactor at 50. The effluent from the evaporator containing crude bisphenol A, phenol, color bodies, and other by-products is fed at 60 to a crystallizer to yield a 1:1 molar adduct complex of phenol and bisphenol A. The mother liquor and the 1:1 adduct are separated in a centrifuge (not shown). The crude bisphenol A, after separation, has a 1:1 molar BPA/phenol crystalline adduct and removed and stripped of phenol and further crystallized to yield high purity bisphenol A product crystals. The mother liquor consisting of a mixture of phenol, BPA isomers and various by-products is then fed at 70 to the rearrangement reactor to increase the yield of para,para-bisphenol A and the resulting product is then fed to the condensation reactor. A line at 80 is shown from the acetone make-up feed to the rearrangement reactor in accordance with the practice of the present invention.

There is also shown at line 70, a purge for reducing unwanted tarry products.

Figure 1:
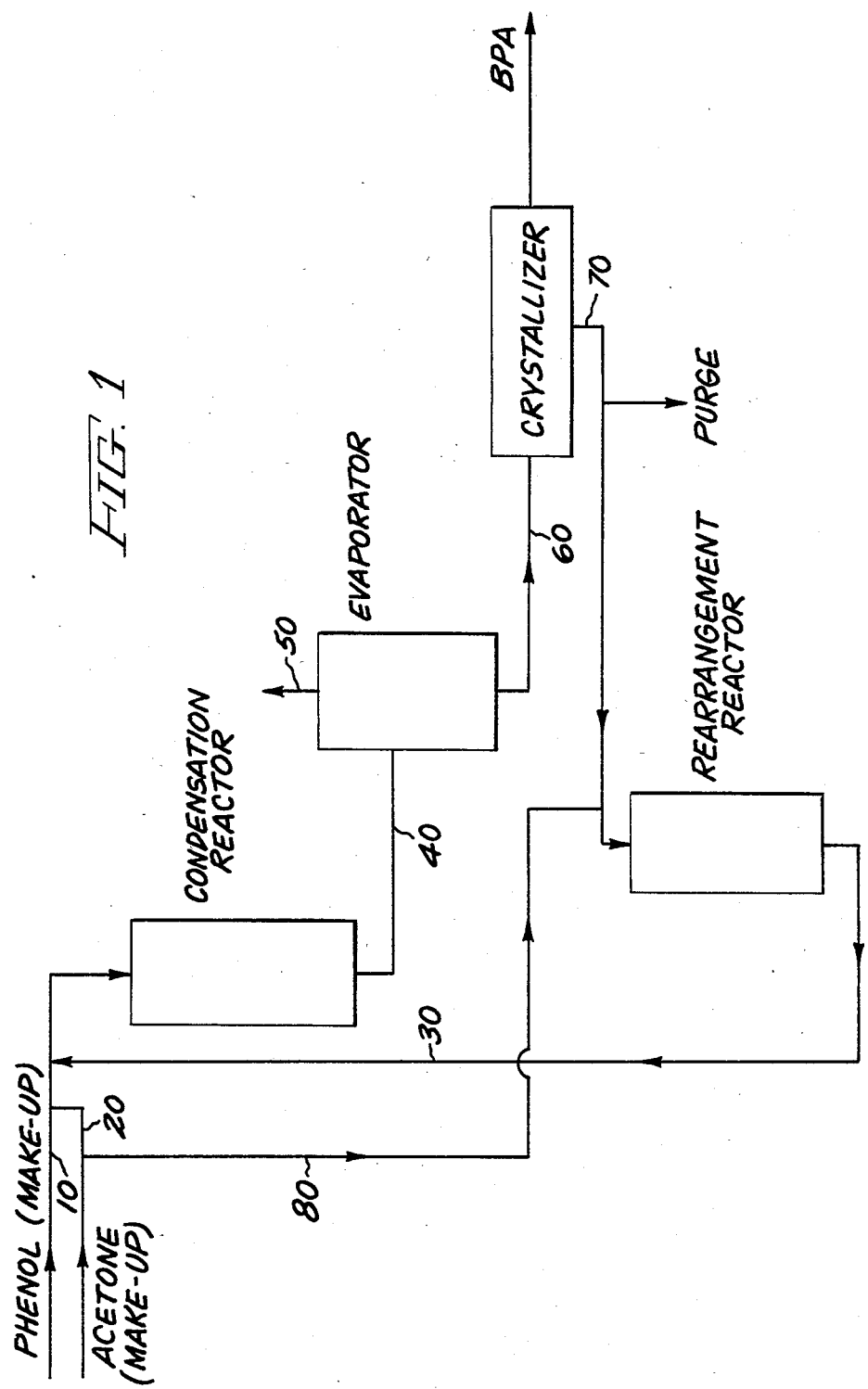
Figure 2:
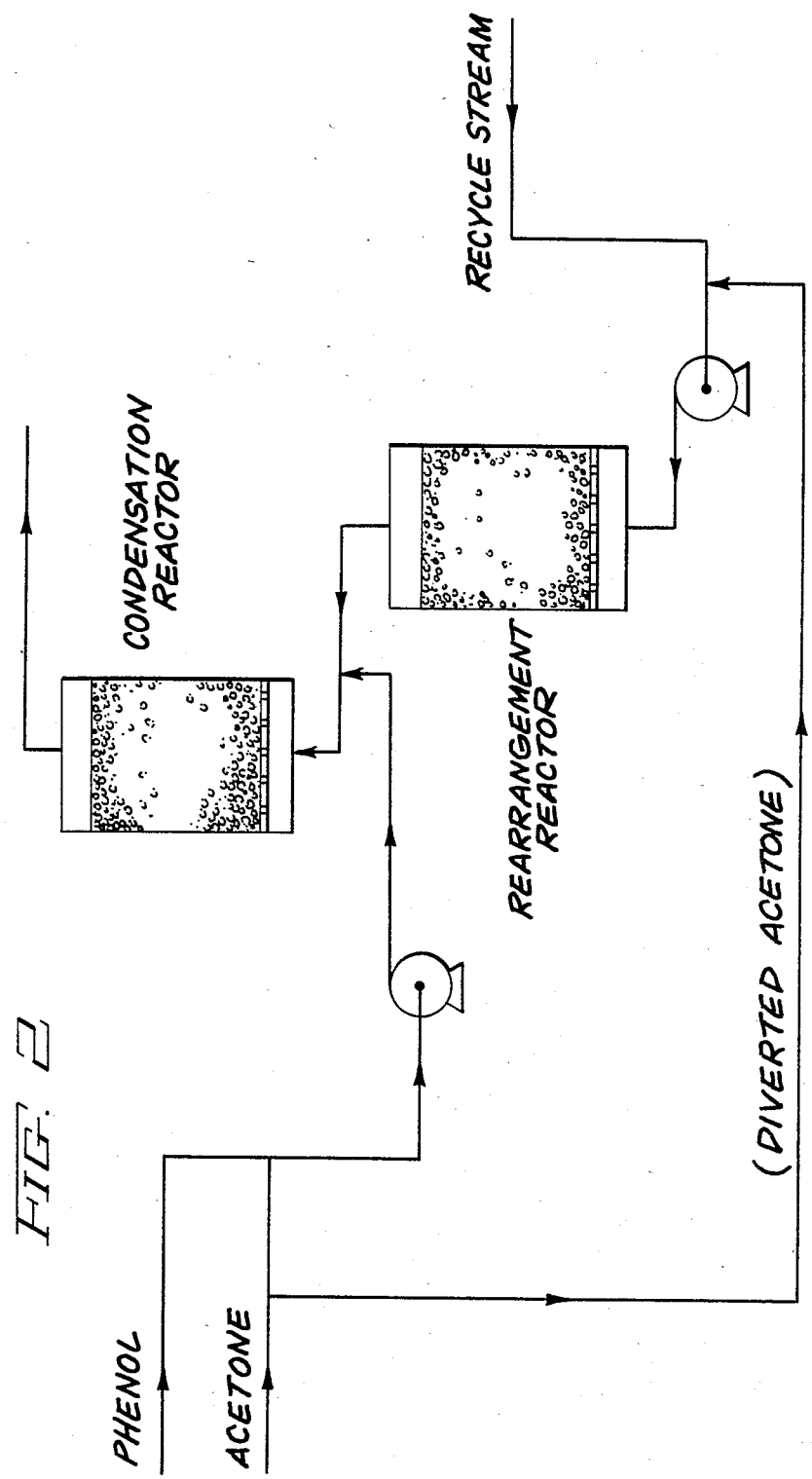

FIG. 2 is a simulated laboratory arrangement used in the example where a recycle stream is fed directly to the rearrangement reactor.

The following example is given by way of illustration and not by way of limitation. All parts are by weight unless otherwise indicated.

EXAMPLE

Two glass tubular vertically positioned reactors (1"×12") were connected as shown in FIG. 2. Each reactor had a perforated disc at its bottom to support an ion exchange bed. Isothermal operation was maintained in each reactor by circulating hot oil through the reactor jacket. One reactor referred to as the "rearrangement reactor" there was used 38 grams of DUOLITE ES-291, which is a macroporous polystyrene divinylbenzene ion exchange resin, having 10% of its acid sites neutralized with 2-mercaptoethylamine. The other reactor, referred to hereinafter as the "condensation reactor", had 14 grams dry weight of a microreticular sulfonated polystyrene divinylbenzene ion exchange resin (Amberlite 118 ®) with about 20% of its acid sites neutralized with 2-mercaptoethylamine.

A synthetic feed mixture was used as the recycle stream. It had the following composition (wt %):
Phenol: 83.21%
p,p-BPA: 12.12%
o,p-BPA: 2.95%
IPP-LD: 0.05%
IPP-CD: 0.56%
BPX-1: 0.52%
Chroman-1: 0.23%
SBI: 0.18%
BPX-2: 0.17%
DMX: 0.01%

The above recycle stream was fed continuously through two reactors injecting phenol and acetone at the inlet of the reactors which were maintained at a temperature of 70° C. Metering pumps were used to control the feed flow rates through the reactors. The feed and the reaction effluent samples were analyzed by high pressure liquid chromatography.

In a control experiment representing the Grover et al. method, U.S. Pat. No. 3,221,061, there was maintained during the run a feed of 114 grams per hour of the recycle stream which was fed into the rearrangement reactor. There was also fed into the condensation reactor 57 grams per hour of phenol, 12.3 grams per hour of acetone and the effluent from the rearrangement reactor. At steady state, an analysis of the condensation reactor effluent was as follows:

| | |
|---|---|
| Total Weight % of Products (p,p-BPA + o,p-BPA + other products) | 22.9% |
| Product Distribution (wt %) (p,p-BPA/o,p-BPA/other products) | 84.2/8.3/7.5 |
| Acetone Conversion (overall, wt %) | 48% |

The same procedure was repeated, except that 30% by weight of acetone was fed into the rearrangement reactor and 70% by weight of acetone was fed into the condensation reactor. The following results were obtained:

| | |
|---|---|
| Total Weight % of Products (p,p-BPA + o,p-BPA + other products) | 25.2% |
| Product Distribution (wt %) (p,p-BPA/o,p-BPA/other products) | 83.9/8.9/7.2 |
| Acetone Conversion (overall, wt %) | 59% |

The above procedure was repeated, except that about 60% of the total acetone feed by weight was fed into the rearrangement reactor and about 40% by weight was fed into the condensation reactor. The following results were obtained:

| | |
|---|---|
| Total Weight % of Products (p,p-BPA + o,p-BPA + other products) | 26.9% |
| Product Distribution (wt %) (p,p-BPA/o,p-BPA/other products) | 82.7/9.3/8.0 |
| Acetone Conversion (overall, wt %) | 65% |

The above results show that diverting about 30% by weight of the acetone to the rearrangement reactor resulted in an increase of about 23% of acetone conversion without any drop in product selectivity. However, when about 60% by weight of the total acetone was diverted to the rearrangement reactor, there was increase of about 35% in acetone conversion, but a noticeable drop was effected in product selectivity was effected. Accordingly, these results show that acetone can be used to enhance acetone conversion without a reduction in product distribution in the overall process if the reaction is operated within the limits of the present invention as previously defined.

Although the above example is directed to only a few of the very many variables which can be used in the practice of the present invention, it should be understood that the present invention is directed to a much broader variation in the weight percents of the reactants utilized in the condensation reactor or rearrangement reactor as well as the use of materials such as ion exchange resins which are shown in the description preceding this example.

What I claim as new and desire to secure by Letters Patent of the United States is:

1. A process for making bisphenol A by feeding phenol and acetone into a condensation reactor at a temperature of about 50° C. to about 120° C. in the presence of an ion exchange catalyst to produce a mixture of bisphenol A, phenol and bisphenol A isomers, which thereafter are separated in a crystallizer to provide the recovery of bisphenol A and the recycling back to the condensation reactor of a mixture of phenol and bisphenol A isomers, through a rearrangement reactor, which comprises the improvement of diverting part of the acetone initially fed to the condensation reactor to the rearrangement reactor, whereby an improvement in overall acetone conversion is achieved, while the product distribution of the condensation reactor effluent is substantially maintained.

2. A method in accordance with claim 1, where the ion-exchange catalyst is neutralized with 10-30% by weight of alkyl mercaptan.

3. A method in accordance with claim 1, where the reaction temperature is 50°-80° C.

4. A method in accordance with claim 1, where about 10-40% of acetone is diverted to the rearrangement reactor based on the total weight of acetone used.

5. A method in accordance with claim 1, where there is used 10 moles of phenol per mole of acetone.

* * * * *